(12) United States Patent
Haddad et al.

(10) Patent No.: US 6,881,538 B1
(45) Date of Patent: Apr. 19, 2005

(54) ARRAY COMPRISING DIAMOND-LIKE GLASS FILM

(75) Inventors: Louis C. Haddad, Mendota Heights, MN (US); Moses M. David, Woodbury, MN (US); Kurt J. Halverson, Lake Elmo, MN (US); Sanjay L. Patil, Minneapolis, MN (US); Jerald K. Rasmussen, Stillwater, MN (US); James I. Hembre, Plymouth, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/519,450

(22) Filed: Mar. 5, 2000

(51) Int. Cl.[7] .............................. C12Q 1/68; C12M 1/36; G01N 15/06; G01B 7/16

(52) U.S. Cl. ..................... 435/6; 435/287.2; 435/287.8; 435/288.7; 435/283.1; 428/216; 427/249; 427/577; 422/50; 422/55; 422/57; 422/68.1; 422/61; 422/69; 422/82.05

(58) Field of Search ...................... 435/6, 287.2, 287.8, 435/288.7, 283.1; 428/216; 427/249, 577; 422/50, 55, 57, 61, 68.1, 69, 82.05

(56) References Cited

U.S. PATENT DOCUMENTS

| | | | |
|---|---|---|---|
| 4,304,705 A | 12/1981 | Heilmann et al. | 260/30.4 |
| 4,332,923 A | 6/1982 | Rainear | 525/507 |
| 4,451,619 A | 5/1984 | Heilmann et al. | 525/379 |
| 4,822,681 A | 4/1989 | Schossler et al. | 428/405 |
| 5,262,484 A | 11/1993 | Coleman et al. | 525/204 |
| 5,278,377 A | 1/1994 | Tsai | 219/759 |
| 5,344,701 A | 9/1994 | Gagnon et al. | 428/304.4 |
| 5,352,492 A | 10/1994 | Dorfman et al. | |
| 5,403,902 A | 4/1995 | Heilmann et al. | 526/260 |
| 5,446,270 A | 8/1995 | Chamberlain et al. | 219/730 |
| 5,466,431 A | 11/1995 | Dorfman et al. | |
| 5,482,830 A * | 1/1996 | Bogart et al. | 435/5 |
| 5,529,708 A | 6/1996 | Palmgren et al. | 252/62.54 |
| 5,718,976 A | 2/1998 | Dorfman et al. | |
| 5,777,372 A * | 7/1998 | Kobashi | 257/414 |
| 5,792,943 A | 8/1998 | Craig | 73/61.52 |
| 5,824,793 A | 10/1998 | Hirschbein et al. | 536/25.34 |
| 5,888,594 A | 3/1999 | David et al. | 427/577 |
| 5,919,626 A | 7/1999 | Shi et al. | 435/6 |
| 5,925,455 A | 7/1999 | Bruzzone et al. | 428/328 |
| 5,976,466 A | 11/1999 | Ratner et al. | 422/82.11 |
| 6,013,789 A | 1/2000 | Rampal | 536/25.3 |
| 6,080,470 A * | 6/2000 | Dorfman | |
| 6,332,363 B1 * | 12/2001 | Molloy et al. | |

FOREIGN PATENT DOCUMENTS

| WO | WO-94/16803 A1 * | 8/1994 |
|---|---|---|
| WO | WO 98/39481 | 9/1998 |
| WO | WO 99/53319 | 10/1999 |
| WO | WO-99/53319 A2 * | 10/1999 |
| WO | WO 01/66820 | 9/2001 |

OTHER PUBLICATIONS

Aebersold et al., "Covalent Attachment of Peptides for High Sensitivity Solid–Phase Sequence Analysis," *Anal. Biochem.*, 187:56–65 (1990).

(Continued)

*Primary Examiner*—W. Gary Jones
*Assistant Examiner*—B J Forman
(74) *Attorney, Agent, or Firm*—Christopher D. Gram; Robert W. Sprague

(57) ABSTRACT

Materials for use in miniaturized arrays, the arrays, and methods of manufacturing. Materials for making arrays described include a substrate with a silicon-containing layer, optionally with linking agents and reactants.

14 Claims, 4 Drawing Sheets

OTHER PUBLICATIONS

David et al., "Plasma Deposition and Etching of Diamond–Like Carbon Films," *AIChE J.*, 37(3):367–376 (1991).

Joos et al., "Covalent Attachment of Hybridizable Oligonucleotides to Glass Supports," *Anal. Biochem.*, 247:96–101 (1997).

Matson et al., "Biopolymer Synthesis on Polypropylene Supports," *Anal. Biochem.*, 217:306–310 (1994).

Mort et al., eds., *Plasma Deposited Thin Films*, CRC Press, Boca Raton, FL, Title Page, publication page and table of contents only, 5 pages (1986).

Rao et al., "Solid Phase Synthesis of the 3'–Terminal Nonadecaribonucleoside Octadecaphosphate Sequence of Yeast Alanine Transfer Ribonucleic Acid," *Tetrahedron Lett.*, 28(41):4897–4900 (1987).

Van Der Voort et al., "Silylation of the Silica Surface A Review," *J. Liq. Chrom. Rel. Technol.*, 19(17&18):2723–2752 (1996).

\* cited by examiner

ARRAY COMPRISING DIAMOND-LIKE GLASS FILM

FIELD OF THE INVENTION

This invention relates to materials for making arrays, the arrays, and methods of manufacturing. The materials and arrays include a polymeric substrate having a silicon-containing layer thereon.

BACKGROUND

Miniaturized arrays may be used in a variety of applications, such as gene sequencing, monitoring gene expression, gene mapping, bacterial identification, drug discovery, and combinatorial chemistry. Many of these applications involve expensive and oftentimes difficult to obtain samples and reagents. Accordingly, miniaturized arrays, which are preferably high density, are desirable because the use of such arrays may dramatically increase efficiency with respect to limited or expensive samples when compared to standard arrays, such as a 96 well plate. For example, a 96 well plate may require several hundred microliters of sample per well to run a diagnostic experiment whereas a miniaturized array would require only a fraction of that sample for the entire array. In addition to the reduction of volume, miniaturization allows hundreds or thousands of tests to be performed simultaneously.

Many methods for manufacturing arrays currently employ the use of glass substrates. Glass is preferred because of its low background fluorescence and relatively low chemical reactivity. However, many methods of manufacturing arrays on glass have other complications, such as how to achieve high densities with precision. Thus, there is a need for additional methods by which arrays can be manufactured, particularly those having high densities of binding sites.

SUMMARY

Significantly, the present invention provides miniaturized arrays that include surfaces that provide the advantages of conventional glass arrays, but are capable of providing a wide range of binding site densities. Surprisingly, arrays can be made according to the present invention from a material having a silicon-containing layer that adheres well upon conversion of the material to an array with a relatively high surface area and high detection signal strength. Such materials are of particular importance because they are capable of being functionalized to alter their surface chemistry using a wide variety of reactants.

Thus, the present invention provides materials that include a substrate having disposed on at least a portion thereof a silicon-containing layer. As used in this context, "disposed thereon" means that the silicon-containing layer is in contact with the substrate, bound or otherwise, or the silicon-containing layer is in contact with one or more intervening layers (e.g., mask layer), bound or otherwise.

Such a layer is preferably capable of silylation, such that linking agents can be covalently bonded to the layer. It is believed that silylation can occur because of the presence of Si—OH groups (i.e., Si—OH moieties), although this is not a necessary requirement. Significantly and advantageously, such linking agents can be those traditionally used in functionalizing silica (e.g., glass) surfaces. This material is suitable for the subsequent affixation of reactants thereto. The linking agents may be provided by functionalizing the silicon-containing layer with a coupling agent, such as a silane coupling agent, or coating a functionalized polymer (i.e., a polymer that includes linking agents) thereon.

The silicon-containing layer can be continuous or discontinuous, as in a patterned layer. Optionally, the arrays, or materials for manufacturing such arrays, can also include polymeric layers, optionally with linking agents, masking layers, and layers of electromagnetic energy sensitive material, for example.

In one embodiment, there is provided a material for use in the manufacture of arrays, the material including a relaxable or recoverable polymeric substrate having disposed on at least a portion thereof a layer that includes silicon atoms (preferably silicon and oxygen, and more preferably silicon, oxygen, and carbon atoms), wherein the layer is capable of undergoing a silylation reaction. The substrate is preferably an oriented film, such as a heat-shrink film, capable of having the orientation relaxed (a "relaxable substrate"), or an elastomeric film that is stretched or capable of being stretched and capable of recovering, preferably to substantially its original size (a "recoverable substrate").

Preferably, the materials for use in the manufacture of arrays, and the arrays themselves, include linking agents for affixing reactants to a silicon-containing layer on a substrate. However, such linking agents are not necessarily required as certain reactants can affix to (e.g., adsorb to) the silicon-containing layer directly. Thus, for certain embodiments, linking agents are disposed on the silicon-containing layer. As used in this context, "disposed" means that the linking agents are directly in contact with the silicon-containing layer (e.g., covalently bonded thereto) or in contact with one or more intervening layers (e.g., an organic polymeric coating). Thus, the linking agents can be provided by a polymeric coating or they can be covalently bonded to the silicon-containing layer, for example.

The silicon-containing layer can be a coating or film, such as a diamond-like glass film. Thus, in a preferred embodiment, the present invention provides a material for use in the manufacture of arrays that includes a relaxable or recoverable polymeric substrate having disposed on at least a portion thereof a diamond-like glass film.

In yet another preferred embodiment, the present invention provides a material for use in the manufacture of arrays that includes a relaxable or recoverable polymeric substrate having disposed on at least a portion thereof a layer that includes, on a hydrogen-free basis, at least about 30% carbon, at least about 25% silicon, and not more than about 45% oxygen. "Hydrogen-free basis" refers to the atomic composition of a material as established by a method such as Electron Spectroscopy for Chemical Analysis (ESCA), which does not detect hydrogen even if large amounts are present in the thin films.

In another embodiment, the present invention provides a material for use in the manufacture of arrays that includes a relaxable or recoverable polymeric substrate having disposed on at least a portion thereof a layer that includes Si—OH groups.

In yet another embodiment, the present invention provides a material for use in the manufacture of arrays that includes a relaxable or recoverable polymeric substrate having disposed on at least a portion thereof a layer that includes silicon atoms (preferably silicon and oxygen atoms, and more preferably silicon, oxygen, and carbon atoms), wherein the layer is covalently bonded to the substrate.

In still another embodiment, the present invention provides a material for use in the manufacture of arrays that includes a relaxable or recoverable polymeric substrate having disposed on at least a portion thereof a layer that includes silicon atoms and linking agents covalently bonded to the silicon-containing layer. Preferably, a reactant is affixed to the linking agents to form an array. More preferably, the reactant forms a binding site.

The present invention also provides arrays. In one embodiment, an array is provided that includes: a polymeric substrate; a silicon-containing layer disposed on at least a portion of the substrate; and a reactant affixed to the silicon-containing layer; wherein the silicon-containing layer has a projected surface area and a topographical surface area, and further wherein the topographical surface area is greater than the projected surface area. Preferably, the silicon-containing layer has linking agents disposed thereon for affixing the reactant thereto. Preferably, the silicon-containing layer includes an undulated surface, although a fractured surface can also be useful.

In another embodiment, an array is provided that includes: a polymeric substrate; a diamond-like glass film disposed on at least a portion of the substrate; and a reactant affixed to the diamond-like film; wherein the diamond-like glass film has a projected surface area and a topographical surface area, and further wherein the topographical surface area is greater than the projected surface area.

Methods of manufacturing such arrays are also provided. In one embodiment, the method includes: providing a relaxable or recoverable polymeric substrate; applying a silicon-containing layer to the polymeric substrate; functionalizing the silicon-containing layer to form linking agents thereon; affixing a reactant to the linking agents; and allowing the substrate to relax or recover, wherein the silicon-containing layer has a topographical surface area and a projected surface area, and further wherein the topographical surface area is greater than the projected surface area.

In one embodiment, the polymeric substrate is an oriented film. For such a substrate, allowing the polymeric substrate to relax or recover involves relaxing it such that it becomes less oriented or isotropic. Preferably, this involves heating the substrate to reduce the orientation. A backing or other structure may be added to retain the substrate in the reduced orientation.

In another embodiment, the polymeric substrate is an elastomeric material. For such a substrate, the method further includes stretching the substrate prior to affixing reactants thereto. Allowing the polymeric substrate to relax or recover involves releasing the stretching force such that the elastomeric material recovers. A backing or other structure may be added to retain the substrate in the stretched state.

Reactants may be affixed to the silicon-containing layer, optionally through linking agents, prior to, during, or subsequent to allowing the substrate to relax or recover to create an array with binding sites. Preferably, the reactants are affixed prior to allowing the substrate to relax or recover.

In another embodiment, a method for manufacturing a blank array includes: providing a relaxable or recoverable polymeric substrate; applying a silicon-containing layer to the polymeric substrate; and functionalizing the silicon-containing layer, thereby creating linking agents on the substrate for subsequent affixation of a reactant thereto. Functionalizing the silicon-containing layer can include coating the layer with a polymeric material that includes linking agents. Alternatively, functionalizing the silicon-containing layer can include covalently bonding a silane coupling agent to the layer. Preferably, the method further includes allowing the substrate to relax or recover, wherein the silicon-containing layer has a topographical surface area and a projected surface area, and further wherein the topographical surface area is greater than the projected surface area.

Various other features and advantages of the present invention should become readily apparent with reference to the following detailed description, examples, claims and appended drawings.

Definitions

The present invention provides miniaturized arrays and methods of manufacturing the same. For purposes of this invention, the following definitions shall have the meanings set forth.

"A" or "an" refers to one or more of the recited elements.

"Affix" shall include any mode of attaching reactants to a silicon-containing layer. Such modes shall include, without limitation, covalent and ionic bonding, adherence, such as with an adhesive, physical entrapment, and adsorption. This may or may not require the use of linking agents.

"Analyte" shall mean a molecule, compound, composition or complex, either naturally occurring or synthesized, to be detected or measured in or separated from a sample of interest. Analytes include, without limitation, proteins, peptides, fatty acids, nucleic acids, carbohydrates, hormones, steroids, lipids, vitamins, bacteria, viruses, pharmaceuticals, and metabolites.

"Binding site" shall mean a discrete location disposed on a silicon-containing layer wherein reactants are affixed thereto. A single binding site may include a quantity of one or more of the same reactants affixed to the silicon-containing layer.

"Density" shall mean a measure of quantity per unit projected area of a silicon-containing layer, such as, for example, linking agents per square centimeter or binding sites per square centimeter.

"Heat-relaxable" or "heat-shrink" shall mean, in the context of a material, such as a substrate, that the material undergoes some relaxation in at least one dimension in response to the transmission of thermal energy into the material.

"Linking agent" shall mean any chemical species capable of affixing a "Reactant" to a silicon-containing layer. Linking agents can be covalently bonded to the silicon-containing layer or provided by a polymeric coating thereon.

"Projected surface area" shall mean the surface area for a surface as is calculated with respect to the plane encompassing the "x" and "y" axes of the surface.

"Reactant" shall mean any chemical molecule, compound, composition or complex, either naturally occurring or synthesized, that is capable of binding an analyte in a sample of interest either alone or in conjunction with a molecule or compound that assists in binding the analyte to the silicon-containing layer, such as, for example, a coenzyme. The reactants of the present invention are useful for chemical or biochemical measurement, detection or separation. Accordingly, the term "Reactant" specifically excludes molecules, compounds, compositions or complexes, such as ink, that do not bind analytes as described above. Examples of reactants include, without limitation, polypeptides (e.g., proteins such as enzymes and antibodies), polynucleotides (e.g., oligonucleotides and cDNA), and carbohydrates.

"Recoverable" means, in the context of a material, such as a substrate, that the material is stretched and capable of subsequently recovering at least one dimension, preferably to substantially its original size.

"Relaxable" shall mean, in the context of a material, such as a substrate, that the material is capable of relaxing, and preferably, shrinking, in at least one dimension. Preferably, shrinkage occurs by at least about 10%.

"Topographical surface area" shall mean the surface area of a surface as is calculated with respect to the planes encompassing the "x", "y" and "z" axes of the surface, or in other words, a measurement of the surface features of the coating.

"Undulations-or-undulated" shall mean convoluted, wave-like forms. For purposes of this invention, it is preferred that an undulated surface includes undulations that are irregular as to pattern, such as depicted in FIGS. 4 and 5. "Undulations-or-undulated" does not include structures such as reservoirs or microwells that are created by methods such as for example printing, embossing, casting, molding, laserscribing, photolithography, etching, mechanical scratching, or scoring.

DETAILED DESCRIPTION OF THE PREFERRED EMBODIMENTS

The present invention provides materials for making miniaturized arrays, and the arrays themselves that include reactive surfaces with high surface areas and high detection signal strength, and methods of manufacturing such arrays. The materials for making the arrays include a relaxable or recoverable substrate on which is disposed a layer that includes silicon atoms. Preferably the layer is directly in contact with the substrate, and more preferably the layer is covalently bonded to the substrate. As used herein, a "layer" includes a film deposited, for example, using plasma deposition techniques, as well as a coating that is first applied to a solid substrate in a liquid state, then solidified by UV radiation (photopolymerizable), heat (thermoset), or by removing solvent molecules from the coating solution.

Preferably, the silicon-containing layer includes silicon and oxygen atoms, and more preferably silicon, oxygen, and carbon atoms. The silicon-containing layer is preferably capable of silylation, such that linking agents can be covalently bonded to the layer. It is believed that silylation can occur because of the presence of Si—OH groups, although this is not a necessary requirement. Optionally, the arrays can also include polymeric layers, optionally with linking agents, masking layers, and layers of electromagnetic energy sensitive material, for example.

Figure 1:
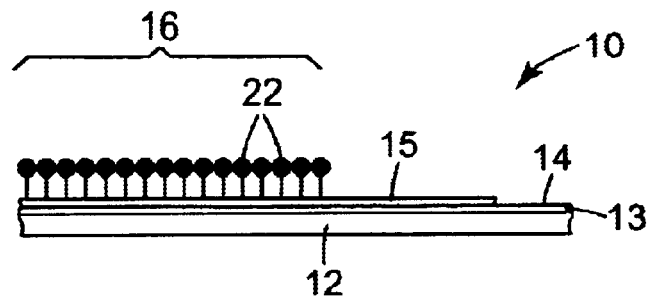
FIG. 1 is side view of an array of the present invention prior to relaxation or recovery of the substrate thereof.
Figure 2:
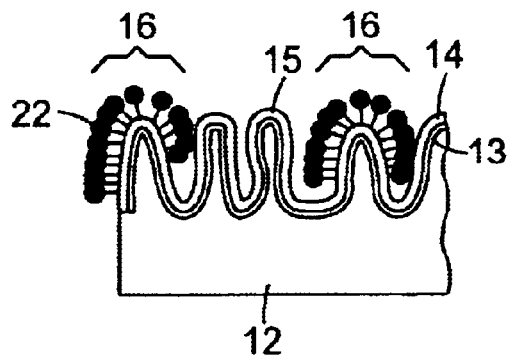
FIG. 2 is a side view of the array of FIG. 1 of the present invention subsequent to relaxation or recovery of the substrate thereof.

With reference to FIGS. 1 and 2, the present invention 10 includes a substrate 12 with at least one major surface 13 having a surface area. The major surface 13 may be generally smooth or may include undulations. The substrate 12 may be any number of shapes. The shape of the substrate 12 is not limiting, so long as the substrate 12 provides a base for applying the silicon-containing layer 15 including linking agents and reactants 22 thereon, as described more fully below.

In a preferred embodiment, the layer 15 is at least partially adhered to the substrate 12, and has a generally smooth appearance. The layer 15 has a projected surface area and a topographical surface area. Accordingly, prior to relaxation of the substrate, the projected surface area and the topographical surface area of the layer 15 are substantially equivalent.

As described more fully below, upon relaxation or recovery of the substrate 12, the topographical surface area of the silicon-containing layer 15 becomes greater than the projected surface area of the silicon-containing layer 15. Surprisingly, an array 10 of the present invention includes silicon-containing layer 15 that is capable of exhibiting topographical surface areas that greatly exceed the projected surface areas. The topographical surface area of the silicon-containing layer 15 is preferably at least about five times greater than the projected surface area. In a most preferred embodiment, the topographical surface area is at least fifteen times greater than the projected surface area.

Figure 6:
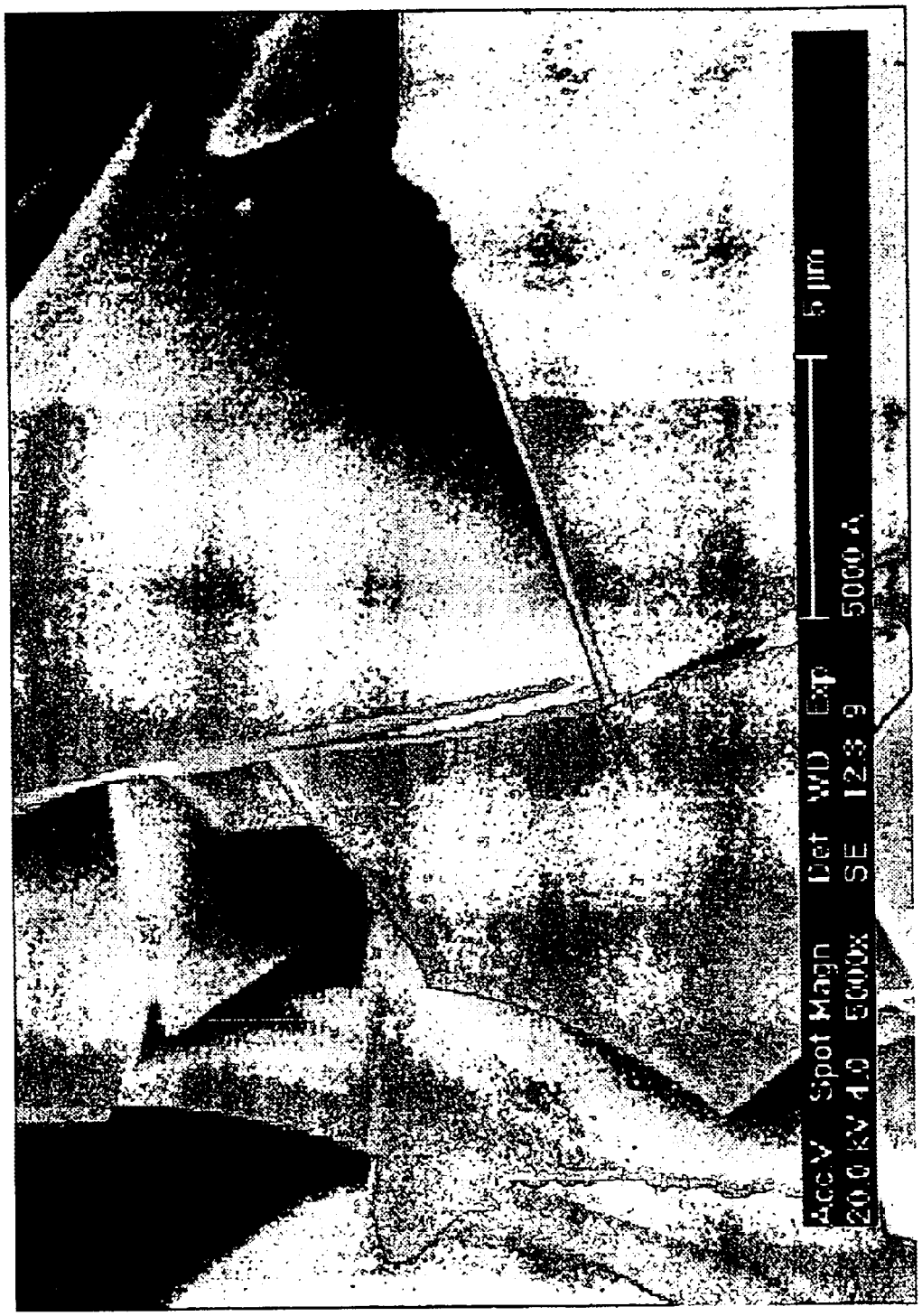
FIG. 6 is a scanning electron micrograph at 5000 magnification of the relaxed surface of a 5000 Angstrom thick silicon-containing layer of a relaxed film as prepared in Example 1D.

In a preferred embodiment, upon relaxation or recovery of the substrate 12, as explained more fully below, the silicon-containing layer 15 becomes undulated as depicted in FIG. 2. While the undulations are irregular with respect to any discernable pattern, it is contemplated that a regular pattern of undulations may be achievable in accordance with the methods of the present invention. The adhesion of the layer 15 to the substrate should be sufficient to prevent its total delamination from the substrate. Because the desired array preferably includes an undulated surface, a degree of delamination may actually occur and still provide a useful array in accordance with the present invention. However, the degree of delamination should not be so great as to interfere with assays being conducted on the arrays or result in effective loss of the silicon-containing layer 15 from the substrate. Surprisingly, the silicon-containing layer 15 may fracture (as shown in FIG. 6), rather than form undulations, and yet not delaminate.

Generally, the silicon-containing layers can be deposited in a variety of thicknesses, depending on the deposition conditions and starting materials. For example, they can be a thin as about 10 Angstroms or as thick as about 10 micrometers (i.e., microns), if desired. Preferably, they are about 200 Angstroms thick to about 1 micron thick. More preferably, they are about 500 Angstroms thick to about 1000 Angstroms thick. It is believed that thicker layers will result in larger-dimensioned undulations because the flexural rigidity of the layer will vary approximately as the cube of its thickness. In theory, a flexurally stiffer object would be expected to bend at a larger radius than that of an object of less rigidity (all other variables being equal). In practice, the flexural rigidity will also be affected by the adhesion properties of the silicon-containing with respect to the substrate.

Arrays of the present invention are capable of exhibiting high topographical surface areas. These high surface area arrays offer additional opportunities for increasing signal strength of the arrays. The undulated and/or fractured surfaces permit more reactants to be affixed to a given area versus binding reactants to a relatively flat surface. Also, in the case where reactants are affixed prior to relaxation or recovery of the substrate, the spatial relationship of the reactants to one another on the surface is fixed. Upon relaxation or recovery of the substrate, the surface of the silicon-containing layer becomes undulated, in effect, increasing the density of reactants with respect to the projected surface area but substantially maintaining their relative separation due to the topographical surface area of the silicon-containing layer. This spacing allows presentation of a high density of reactants or binding sites at or near the surface of the silicon-containing layer while minimizing potential steric crowding. This, in turn, facilitates rapid interaction kinetics with prospective analytes.

Substrates

The substrate of the present invention is a polymeric material. The material of the substrate is selected with regard to the application for the resulting arrays. For example, the substrate preferably exhibits low background fluorescence in the event fluorescence is used for detection purposes and therefore will not substantially interfere with the indicator systems used in the assays run on the arrays manufactured in accordance with the methods of the present invention. The substrate material preferably is compatible with the reagents and conditions of the assays, such as temperature and pH.

Many polymeric materials may be suitable for use in the present invention. However, in order to form the high surface area surface preferred, the materials are preferably capable of being oriented, i.e., films that shrink at least in one direction within the film plane when energy, preferably heat, is applied to the film for a specified period of time. Elastomeric materials, which are stretched at least in one direction prior to affixation of reactants, constrained in the stretched state during affixation of reactants, and then allowed to recover, thereby reducing the projected surface area of the substrate surface from the stretched state, are also suitable for use in the present invention. Thus, herein, a relaxable substrate includes an oriented film and a recoverable substrate includes an elastomeric material.

With respect to oriented films, shrinkage need not be equal in any two orthogonal directions within the film plane, although a substantially uniform shrinkage is preferred. In considering shrinkage as a function of direction in the film plane, substantial uniformity of directionally-dependent shrinkage from point to point within the film is preferred; that is, the oriented film preferably shrinks in substantially the same amount in each direction, regardless of position on the film plane. If the oriented film employed does not exhibit substantially uniform shrink characteristics, a registration indicator may be added to the binding sites or otherwise employed to register the binding sites in the finished array.

While the starting substrate material of the present invention includes oriented films, the substrates of the arrays of the present invention are generally relaxed, i.e., generally no longer oriented or, in fact, isotropic. A backing may be applied to the substrate to maintain the substrate in a less than oriented state. The backing may optionally include a release liner to permit the backing to be removed if desired.

The substrate provides a preferably non-porous surface upon which silicon-containing layers, or other films or coatings (e.g., polymeric coatings, mask layers, etc.) may be disposed. Upon relaxation or recovery of the substrate, the substrate provides support and integrity to the silicon-containing layer, or other films or coatings (e.g., polymeric coatings, mask layers, etc.) disposed thereon.

Preferred oriented films include biaxially oriented low-density polyethylenes; biaxially oriented linear low-density polyethylenes; and biaxially oriented ultra low-density polyethylenes. Biaxially oriented films are preferred because they exhibit shrinkage in two orthogonal in-plane directions (hereafter referred to as the "x" and "y" directions). Other oriented films that may be suitable for use in the present invention include uniaxially, biaxially, or multiaxially oriented films made by any process known to the art, including, but not limited to: melt-orientation; the blown film, bubble, double-bubble, and tubular processes; length orientation; the process of tentering; extension over a mandrel; thermoforming; and blow molding. Polymers which may be employed in such films include, but are not limited to: polyethylenes, including high density polyethylene, low density polyethylene, linear low density polyethylene, ultra low density polyethylene, and copolymers of ethylene (including ethylene propylene copolymers and ethylene vinyl acetate copolymers); polyolefins, including isotactic polypropylene, syndiotactic polypropylene, and polymethylpentene; polyacetals; polyamides, including polyamide 6 and polyamide 66; polyesters, including polyethylene terephthalate, polybutylene terephthalate, and polyethylene naphthalate; halogenated polymers, including polyvinyl chloride, polyvinylidene chloride, polychlorotrifluoroethylene, polyvinyl fluoride, and polyvinylidene fluoride; styrene polymers, including general purpose polystyrene and syndiotactic polystyrene; cellulose esters, including cellulose acetate and cellulose propionate; polyketones, including polyetheretherketone and copolymers and terpolymers of carbon monoxide with ethylene and/or propylene; polycarbonates, including the polycarbonate of bisphenol A; phenyl-ring polymers, including polyphenylene sulfide; polysulfones; polyurethanes; polymers of acrylic and methacrylic acids and their esters; ionomers; and copolymers, blends, or layered structures of any of the above-named polymers. Oriented films of any of these polymers may be optionally cross-linked.

Examples of elastomeric materials that may be suitable for use in the present invention include natural rubber, polyisoprenes, polychloroprene, polyisobutylenes, polybutenes, nitrites, polyurethanes, silicones, random copolymers and terpolymers (such as ethylene-propylene copolymers and ethylene-propylene-diene monomer terpolymers), and block copolymers.

Silicon-Containing Layers

The silicon-containing layer in the arrays of the present invention, or materials for manufacturing such arrays, is preferably capable of silylation such that linking agents can be covalently bonded to the layer. It is believed that silylation can occur because of the presence of Si—OH groups, although this is not a necessary requirement. Significantly and advantageously, such linking agents can be those traditionally used in functionalizing silica (e.g., glass) surfaces. This material is suitable for the subsequent affixation of reactants thereto, although linking agents are not necessarily required for affixing reactants to the silicon-containing layer. The linking agents may be provided, for example, by functionalizing the silicon-containing layer with a coupling agent, such as a silane coupling agent, or coating a functionalized polymer thereon (e.g., azlactone-functional polymers described below).

The silicon-containing layer can be a film or a coating. Films typically include plasma and/or vapor deposited materials containing silicon atoms, such as silicon oxide films, silicon nitride films, silicon oxynitride films, plasma polymerized polysiloxane films, hydrogenated and nonhydrogenated amorphous silicon-containing films, silicon-doped diamond-like carbon films, and the like. See, for example, Applicants' Assignee's copending applications U.S. Ser. No. 09/519,449, filed on even date herewith and U.S. Ser. No. 09/519,447, filed on even date herewith; and *Plasma Deposited Thin Films,* J. Mort & F. Jansen, Eds.; CRC Press, Boca Raton, Fla. (1986). Coatings typically include materials containing silicon atoms deposited from a liquid, such as polysiloxanes, silicon oxides formed from hydrolysis reactions, and the like. Such silicon-containing layers provide a surface that can mimic silica (e.g., glass) substrates with respect to reactivity and interaction with linking agents and reactants.

Preferred silicon-containing layers include diamond-like glass films. As the term is used herein, "diamond-like glass film" refers to substantially or completely amorphous films including carbon, silicon, and oxygen. The films may be covalently coupled or interpenetrating. The amorphous diamond-like films of this invention may contain clustering of atoms that give a short-range order but are essentially void of medium and long range ordering that lead to micro or macro crystallinity which can adversely scatter actinic radiation having wavelengths of from 180 nm to 800 nm. Diamond-like glass (DLG) includes an amorphous carbon system with a substantial quantity of silicon and oxygen, as in glass, yet still retains diamond-like properties. In these films, on a hydrogen-free basis, there is at least about 30% carbon, a substantial amount of silicon (at least about 25%) and not more than about 45% oxygen (references to compositional percentages herein refer to atomic percents). The unique combination of a fairly high amount of silicon with a significant amount of oxygen and a substantial amount of carbon makes these films highly transparent and flexible (unlike glass).

Thin films made in accordance with the invention may have a variety of light transmissive properties. Depending upon the application, the thin films may have increased transmissive properties at various frequencies. However, in specific embodiments the thin film is at least about 50 percent transmissive to radiation at one or more wavelength of about 180 to about 800 nanometers.

Diamond thin films having significantly different properties from the amorphous diamond-like film of the present invention due to the arrangement and intermolecular bonds of carbon atoms in the specific material, have previously been deposited on substrates. The type and amount of intermolecular bonds are determined by infrared (IR) and nuclear magnetic resonance (NMR) spectra. Carbon deposits contain substantially two types of carbon-carbon bonds: trigonal graphite bonds ($sp^2$) and tetrahedral diamond bonds ($sp^3$). Diamond is composed of virtually all tetrahedral bonds, while amorphous diamond-like films are composed of approximately 50% to approximately 90% tetrahedral bonds, and graphite is composed of virtually all trigonal bonds.

The crystallinity and the nature of the bonding of the carbonaceous film determines the physical and chemical properties of the deposit. Diamond is crystalline, whereas the amorphous diamond-like films of the invention are a non-crystalline, amorphous material, as determined by x-ray diffraction. Diamond is essentially pure carbon, whereas diamond-like films can contain a substantial amount of additional components (up to approximately 50 atomic percent for a single non-carbon component, and up to approximately 75 atomic percent for the combination of all additional non-carbon components). These atomic percents can be determined by combustion analysis.

Diamond has the highest packing density, or gram atom density (GAD), of any material at ambient pressure. Its GAD is 0.28 gram atoms/cc. Amorphous diamond-like films have a GAD ranging from about 0.20 to 0.28 gram atoms/cc. In contrast, graphite has a GAD of 0.18 gram atoms/cc. The high packing density of amorphous diamond-like films affords excellent resistance to diffusion of liquid or gaseous materials. Gram atom density is calculated from measurements of the weight and thickness of a material. "Gram atom" refers to the atomic weight of a material expressed in grams.

Amorphous diamond-like films are diamond-like because, in addition to the foregoing physical properties that are similar to diamond, they have many of the desirable performance properties of diamond such as extreme hardness (1000 to 2000 kg/mm$^2$), high electrical resistivity ($10^9$ to $10^{13}$ ohm-cm), a low coefficient of friction (0.1), and optical transparency over a wide range of wavelengths (an extinction coefficient of less than 0.1 in the 400 to 800 nanometer range).

Diamond films, as opposed to diamond-like films, also have some properties, which in many applications make them less beneficial as a protective layer than amorphous diamond-like films. Diamond films have grain structures, as determined by electron microscopy. The grain boundaries are a path for chemical attack and degradation of the substrates, and also cause scattering of actinic radiation. Amorphous diamond-like films do not have a grain structure, as determined by electron microscopy, and are thus well suited to applications wherein actinic radiation will pass through the film.

The polycrystalline structure of diamond films causes light scattering from the grain boundaries. Surprisingly, diamond-like films in accordance with the invention allow for excellent light transmission. Additionally, the visible light transmission of a carbon-, or carbon- and hydrogen-, based film is further improved by incorporating silicon and oxygen atoms into the amorphous diamond-like structure during the deposition process. This is not possible for crystalline diamond thin films because additional components will disrupt its crystalline lattice structure.

Diamond-like films can be deposited in a variety of thicknesses, depending on the deposition conditions and starting materials. For example, they can be a thin as about 10 Angstroms or as thick as about 10 micrometers (i.e., microns), if desired. Preferably, they are about 200 Angstroms thick to about 1 micron thick. More preferably, they are about 500 Angstroms thick to about 1000 Angstroms thick.

Regardless of how thick the film is, the diamond-like glass film typically has an extinction coefficient of less than 0.002 at 250 nm and more typically less than 0.010 at 250 nm. Also, diamond-like glass films usually have a refractive index greater than 1.4 and sometimes greater than 1.7. Diamond-like glass films show low levels of fluorescence, typically very low, and sometimes low enough that they show no fluorescence. Preferably, the diamond-like glass film has fluorescence comparable, nearly equal, or equal to that of quartz.

Adhesion of the diamond-like film to the substrate may be improved, if desired, by any of the methods known to one skilled in the art. These methods typically include various pre-treatments such as corona or plasma treatment.

Method for Forming Diamond-Like Films

The diamond-like films are deposited by plasma deposition onto substrates from gases using the methods and apparatus disclosed in Applicants' Assignee's copending applications U.S. Ser. No. 09/519,449, filed on even date herewith and U.S. Ser. No. 09/519,447, filed on even date herewith.

A typical system includes electrodes one or both of which are powered by RF and a grounded reaction chamber. A substrate is placed proximate the electrode and an ion sheath is formed around the powered electrode to establish a large electric field across the ion sheath. Plasma is generated and sustained by means of a power supply (an RF generator operating at a frequency in the range of about 0.001 Hz to about 100 MHz). To obtain efficient power coupling (i.e., wherein the reflected power is a small fraction of the incident power), the impedance of the plasma load can be matched to the power supply by means of matching network that includes two variable capacitors and an inductor, which is available from RF Power Products, Kresson, N.J., as Model # AMN 3000.

Briefly, the grounded reaction chamber is partially evacuated, and radio frequency power is applied to one of two electrodes. A carbon-containing source is introduced between the electrodes to form a plasma that includes reactive species in proximity to the electrodes, and to also form an ion sheath proximate at least one electrode. The substrate is exposed to the reactive species within the ion sheath that is proximate an electrode to form a diamond-like thin film on the substrate.

Deposition occurs at reduced pressures (relative to atmospheric pressure) and in a controlled environment. A carbon-rich plasma is created in a reaction chamber by applying an electric field to a carbon-containing gas. Substrates on which a film is to be deposited are usually held in a vessel or container in the reactor. Deposition of the diamond-like film typically occurs at rates ranging from about 1 nanometer per second (nm/second) to about 100 nm/second (about 10 Angstroms per second to about 1000 Angstoms per second), depending on conditions including pressure, power, concentration of gas, types of gases, relative size of electrodes, etc. In general, deposition rates increase with increasing power, pressure, and concentration of gas, but the rates will approach an upper limit.

Species within the plasma react on the substrate surface to form covalent bonds, resulting in an amorphous diamond-like film on the surface of the substrates. A multiplicity of substrates may simultaneously have a film deposited on them during the process of this invention. The substrates can be held in a vessel or container within an evacuable chamber that is capable of maintaining conditions that produce diamond-like film deposition. That is, the chamber provides an environment that allows for the control of, among other things, pressure, the flow of various inert and reactive gases, voltage supplied to the powered electrode, strength of the electric field across the ion sheath, formation of a plasma containing reactive species, intensity of ion bombardment and rate of deposition of a diamond-like film from the reactive species.

Prior to the deposition process, the chamber is evacuated to the extent necessary to remove air and any impurities. Inert gases (such as argon) may be admitted into the chamber to alter pressure. Once the substrate is placed in the chamber and it is evacuated, a substance containing carbon (and usually hydrogen), and optionally a substance from which an additional component can be deposited, is admitted into the chamber and, upon application of an electric field, forms a plasma from which the amorphous diamond-like film is deposited. At the pressures and temperatures of diamond-like film deposition (typically, about 0.13 Pascal (Pa) to about 133 Pa (0.001 to 1.0 Torr) (all pressures stated herein are gauge pressure) and less than 50° C.), the carbon-containing substances and substances from which an optional additional component may be obtained will be in their vapor form.

For the deposition of carbon and hydrogen in a diamond-like film, hydrocarbons are particularly preferred, including acetylene, methane, butadiene, benzene, methylcyclopentadiene, pentadiene, styrene, naphthalene, and azulene. Mixtures of these hydrocarbons may also be used. Gases containing optional additional components can also be introduced into the reaction chamber. Gases with low ionization potentials, i.e., 10 eV or less, typically are used for efficient deposition of the diamond-like film. Sources of silicon include silanes such as $SiH_4$, $Si_2H_6$, tetramethylsilane, and hexamethyldisiloxane. Sources of oxygen include oxygen gas ($O_2$), hydrogen peroxide ($H_2O_2$), water ($H_2O$), and ozone ($O_3$).

The additional optional diamond-like film components, including one or more of hydrogen, nitrogen, oxygen, fluorine, silicon, sulfur, titanium, or copper, may be introduced in vapor form into the reaction chamber during the deposition process. Typically, even when the sources for the additional components are solids or fluids, the reduced pressure in the deposition chamber will cause the source to volatilize. Alternatively, the additional components may be entrained in an inert gas stream. The additional components may be added to the chamber while a carbon- or hydrocarbon-containing gas is sustaining the plasma and/or may be added to the chamber after the flow of carbon or hydrocarbon-containing gas has been stopped.

The electrodes may be the same size or different sizes. If the electrodes are different sizes, the smaller electrode will have a larger ion sheath (regardless of whether it is the grounded or powered electrode). This type of configuration is referred to as an "asymmetric" parallel plate reactor. An asymmetric configuration produces a higher voltage potential across the ion sheath surrounding the smaller electrode. Establishing a large ion sheath on one of the electrodes is preferred for this invention because the substrate is preferably located within an ion sheath to benefit from the ion bombardment effects that occur within the sheath.

Preferred electrode surface area ratios are from 2:1 to 4:1, and more preferably from 3:1 to 4:1. The ion sheath on the smaller electrode will increase as the ratio increases, but beyond a ratio of 4:1 little additional benefit is achieved. The reaction chamber itself can act as an electrode. A preferred configuration for this invention includes a powered electrode within a grounded reaction chamber that has two to three times the surface area of the powered electrode.

In an RF-generated plasma, energy is coupled into the plasma through electrons. The plasma acts as the charge carrier between the electrodes. The plasma can fill the entire reaction chamber and is typically visible as a colored cloud. The ion sheath appears as a darker area around one or both electrodes. In a parallel plate reactor using RF energy, the applied frequency is preferably in the range of about 0.001 Megaherz (MHz) to about 100 MHz, preferably about 13.56 MHz or any whole number multiple thereof. This RF power creates a plasma from the gas (or gases) within the chamber. The RF power source can be an RF generator such as a 13.56 MHz oscillator connected to the powered electrode via a network that acts to match the impedance of the power supply with that of the transmission line and plasma load (which is usually about 50 ohms so as to effectively couple the RF power). Hence this is referred to as a matching network.

The ion sheath around the electrodes causes negative self-biasing of the electrodes relative to the plasma. In an asymmetric configuration, the negative self-bias voltage is negligible on the larger electrode and the negative bias on the smaller electrode is typically in the range of 100 to 2000 volts. While the acceptable frequency range from the RF power source may be high enough to form a large negative direct current (DC) self bias on the smaller electrode, it should not be high enough to create standing waves in the resulting plasma, which is inefficient for the deposition of a transmissive diamond-like film.

For planar substrates, deposition of dense diamond-like thin films can be achieved in a parallel plate reactor by placing the substrates in direct contact with a powered electrode, which is made smaller than the grounded electrode. This allows the substrate to act as an electrode due to capacitive coupling between the powered electrode and the substrate. This is described in M. M. David et al., *AIChE Journal,* 37, No. 3, p. 367 (1991).

Linking Agents and Reactants

In certain embodiments, the silicon-containing layers can include linking agents, and optionally reactants, to modify the chemistry of the surface. The linking agents may be substantially over the entire area of a surface of the silicon-containing layer, or in spots that may be in a regular or irregular pattern on such surface (as in a discontinuous layer). If desired, more than one type of linking agent may be used.

Reactants can be affixed to the silicon-containing layer, which is disposed on a substrate, to create binding sites. As described more fully below, with respect to the methods of the present invention, any number of processes known in the art may be used to introduce the reactants to be affixed to the silicon-containing layer. It is understood that the mode of affixation may vary in accordance with the reactant or reactants employed.

The type of reactant used in the present invention will vary according to the application and the analyte of interest. For example, when characterizing DNA, oligonucleotides are preferred. When conducting diagnostic tests to determine the presence of an antigen, antibodies are preferred. In other applications, enzymes may be preferred. Accordingly, suitable reactants include, without limitation, polypeptides (e.g., proteins such as enzymes and antibodies), polynucleotides (e.g., nucleic acids, oligonucleotides, cDNA), and carbohydrates. Preferred reactants include proteins, nucleic acids, and carbohydrates.

Figure 3:
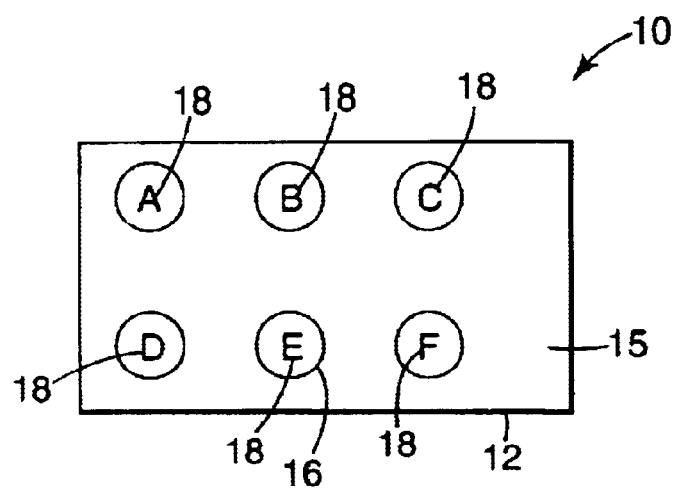
FIG. 3 is a perspective view of an oligonucleotide array manufactured in accordance with the methods of the present invention wherein each letter represents a different oligonucleotide.

Reactants 22 are affixed to the silicon-containing layer 15 to create binding sites 16 as generally depicted in FIGS. 1, 2, and 3. As described more fully below, with respect to the methods of the present invention, any number of processes known in the art may be used to introduce the reactants to be affixed to the silicon-containing layer. It is understood that the mode of affixation may vary in accordance with the reactant or reactants employed.

With reference to FIG. 3, in a preferred embodiment, a variety of nucleic acids, such as oligonucleotides 18 (an oligonucleotide being denoted by a letter) are affixed to the silicon-containing layer 15 at separate binding sites 16. The variety of oligonucleotides 18 on the silicon-containing layer 15 permits a large number of potential binding events between reactants and target analytes in a sample.

The reactants may be affixed prior to, during, or after relaxation or recovery of the substrate. However, it is preferred to affix the reactants prior to relaxation or recovery of the substrate in order to take advantage of the methods of the present invention wherein high reactant binding site densities may be achieved.

Methods of Relaxation/Recovery and Functionalization

Shrinkage of the films can be accomplished using the methods described in International Publication No. WO 99/53319, published Oct. 21, 1999. Oriented films exhibit an area shrinkage reduction that is dependent in part on the degree of elongation of the film during orientation thereof. The area shrinkage reduction is a measure of the area shrinkage of the film from its oriented, pre-shrunken dimensions to its dimensions after energy has been applied to shrink the film. For example, a 10 cm×10 cm (100 $cm^2$ area) film that shrinks fifty percent (50%) in the "x" direction and fifty percent (50%) in the "y" direction after the application of sufficient heat will be reduced to 5 cm×5 cm (25 $cm^2$ area), thereby exhibiting an area shrinkage reduction of seventy-five percent (75%). An area shrinkage reduction of about twenty-five percent (25%) is suitable for use in the present invention with an area shrinkage reduction of more than about seventy-five percent (75%) being most preferred because films exhibiting area shrinkage reductions of this magnitude are capable of achieving very high-density arrays, as more fully described below.

In the case of elastomeric materials, the substrate is stretched in the "x" and/or "y" direction and retained in the stretched condition. Processes for stretching an elastomeric material may include using a tentering device or stretching the material over a frame or mandrel. In most applications, a uniform stretching of the substrate in both the "x" and "y" configuration is preferred so that reactants may be affixed in parallel rows. However, other patterns of reactants may be desired, such as, for example, a fan shape array of reactants. Accordingly, the extent and pattern of stretching may be dependent on the desired shape of the finished array.

The silicon-containing layer need not be functionalized in order to affix reactants thereto. However, depending on the mode of affixation, it may be desirable to functionalize the silicon-containing layer to create linking agents.

The type of functionalization will depend on the type of reactant(s). Preferably, a variety of conventional approaches to rendering the surfaces of silica (e.g., glass) materials chemically reactive are known and may be employed in the present invention to the extent their use creates linking agents on the silicon-containing layer for subsequent affixation of reactants. These include using silane coupling agents such as amino silanes to provide amino functionality, carboxy silanes to provide carboxy functionality, epoxy silanes to provide epoxy functionality, mercapto silanes (e.g., those of the formula HS-L-Si(X)(Y)(Z) wherein L is divalent organic linking group, X is a hydrolyzable group such as alkoxy, acyloxy, amine or chlorine, Y and Z are hydrolyzable or nonhydrolyzable groups) to provide mercapto functionality, hydroxy silanes, such as glycidoxypropyl silanes, to provide hydroxy functionality, and the like. Conditions of such silylation reactions (i.e., silanization reactions) are generally known to one of skill in the art. Examples of other silylation reactions are described in Van Der Voort et al., *J. Liq. Chrom. & Rel Rechnol.,* 19, 2723–2752 (1996); Sudhakar Rao et al., *Tet. Lett.,* 28, 4897–4900 (1987); Joos et al., *Anal. Biochem.,* 247, 96–101 (1997); Aebersold et al., *Anal. Biochem.,* 187, 56–65 (1990); and International Publication No. WO 98/39481, published Sep. 11, 1998.

Any number of processes known in the art may be used to introduce the reactants, including on-chip or off-chip synthesis. Using such techniques, the methods of the present invention can be used to increase array site density by greater than a factor of twenty. For the purpose of high throughput manufacturing, however, sophisticated miniaturized tools and methods, such as those used in on-chip and off-chip synthesis, may not be desired. Accordingly, large quantities of reactants may be deposited in a short period of time because the initial substrate size is relatively large, such as a substrate having a 4 cm×4 cm surface. The resulting binding sites formed may be relatively large, with areas, for example, of approximately 0.25 mm² to 1.0 mm² being suitable for use in the present invention. For example, the solutions containing the reactants to be affixed may be simultaneously introduced by arrays of capillary tubes, by arrayed pipetting devices, or by an array of posts designed to transfer liquid droplets from a tray of reservoirs.

It is preferred that the reactants be introduced to the silicon-containing layer in a known pattern for purposes of registration. The initial starting position of the reactant should be known in order to correlate this position with the final position once the substrate size has been reduced to the dimension which will be employed in conducting the assay. Each binding site may include a dye to assist in the correlation between initial starting point and the end point. Preferably, the dye has a different detection mode, e.g., light source, wavelength, etc., than the dye or indicator used for purposes of detecting binding events on the array.

After affixation of the reactant(s) to the silicon-containing layer, the substrate is relaxed, as in the case of an oriented film, or recovered, as in the case of a stretched elastomeric material. The number of binding sites before and after size reduction is equivalent. However, the increase in density of reactants, binding sites and linking agents, if present, may be dramatic.

The arrays manufactured in accordance with the methods of the present invention are capable of having binding site densities of over 1,000 per cm². A preferred density is at least 25,000 per cm² and a most preferred density is over 60,000 per cm². Accordingly, the methods of the present invention permit the manufacturer to increase the density of binding sites from the initial affixation of reactants to the size reduced state by fairly substantial factors, such as 4, 10, and even over 20. The area of each binding site can be reduced by these same factors, thereby creating an increased density of reactant at each site. This increased density of reactant is advantageous where an increased signal for detection is desired when conducting an assay, for example, when fluorescent, absorbent, or chemiluminescent species are used as reporters.

With respect to oriented films, the reduction is preferably effected by the application of heat, although other modes of relaxing oriented films can be used. Preferably, the mode of size alteration, such as the application of heat, does not substantially impair the activity of the reactants. It is believed that fairly high heat may be employed to shrink a substrate having oligonucleotides affixed thereto (approximately 150 degrees Celsius) without destroying the ability to have subsequent DNA hybridization occur with the oligonucleotides.

With respect to elastomeric materials, the surface area reduction may be achieved by releasing the force that is holding the material in the stretched condition. The substrate may be subsequently treated to hold the substrate in the reduced format. Alternatively, a backing or other physical means may be applied to the substrate to hold it in the size altered format.

After size alteration of the substrate, the substrate, if desired, may be treated to retain the substrate in the reduced surface area state. Such treatment includes cross-linking the substrate. Alternatively, physical modes may be used, such as applying a backing to the substrate.

Optional Polymeric Coatings

The arrays of the present invention can include polymeric coatings, typically overlying the silicon-containing layers, if desired. Such polymeric coatings can provide a variety of linking agents on the silicon-containing layer. Alternatively, they can be applied to a silicon-containing layer that already includes linking agents.

Examples of polymeric coatings include those that are suitable for affixing reactants and are compatible with the assays and attendant conditions that are to be conducted on the particular array, such as those described in International Publication No. WO 99/53319; published Oct. 21, 1999. Preferred linking agents are azlactone moieties such as those provided by copolymers as taught in U.S. Pat. Nos. 4,304,705; 4,451,619; 5,262,484; 5,344,701; and 5,403,902. Especially preferred copolymers are those prepared using hydrophilic or water-soluble comonomers such as acrylamide and acrylamide derivatives, hydroxyethylacrylate and methacrylate, and the like. In addition to azlactone linking agents, copolymers including other linking agents may also be utilized. These include, for example, epoxy, carboxylic acid, hydroxyl, amine, N-hydroxysuccinimide, iso- and isothiocyanate, anhydride, aldehyde, and other groups which are well known in the art for the immobilization of reactants. The copolymers comprising linking agents may be prepared by either step growth or chain growth polymerization processes as are well known in the art.

Azlactone moieties are preferred because these moieties are suitable for reaction with numerous reactants, including oligonucleotides as exemplified in International Publication No. WO 99/55319, published Oct. 21, 1999. Azlactone moieties are generally hydrolytically stable and therefore have a relatively long shelf life when used in applications of the present invention. These moieties also generally exhibit high reactivity with a wide variety of reactants.

The coatings may be crosslinked or otherwise treated to insolubilize, modify the $T_g$, or modify the adhesion properties of the coating. For example, copolymers that have a low $T_g$ may be formulated with a crosslinker in order to raise the $T_g$ of the resultant coating. The coatings can be applied by any of several conventional means known in the art, such as extrusion coating, die coating, dip coating, air-knife coating, gravure coating, curtain coating, spray coating, use of wire wound coating rods, and the like. Coatings may be made from solution, followed by removal of solvent, or by hot melt coating of 100% solids formulations.

A first coating of linking agents may be overcoated by a second coating of linking agents in order to obtain undulations in accordance with the methods of the present invention. In this manner, a coating that would otherwise not form undulations may be converted to an undulated coating. Preferably, the two coatings would adhere to each other or chemically bond to each other. For example, the substrate may be coated with a polymer including azlactone moieties that in turn are overcoated with a second polymer including amine moieties. The amines and azlactone would react to bind the layers together, however, it is anticipated that free amine groups would remain to affix reactants, such as cDNA, to the substrate.

Optional Masking Layers

In some instances, mask layers are used to reduce or prevent transmission of the excitation energy through the mask layer to the underlying substrate, as disclosed in U.S. patent application Ser. No. 09/410,863, filed on Oct. 1, 1999. In other instances, mask layers are used to reduce or prevent the transmission of electromagnetic energy from beneath the analyte, e.g., the substrate, that is similar to the electromagnetic signal emitted by the desired analyte in response to the excitation energy. In either case, with the mask layer in place, the electromagnetic signals emitted from the surface of the array can generally be attributed to excitation of the analyte captured on the array, rather than the underlying substrate or other portions of the array. Referring to FIG. 1, the optional mask layer 14 preferably underlies the silicon-containing layer 15.

The mask layer materials can be selected based on two characteristics. Those characteristics include the optical density of the mask layer and the ability to form an undulated surface on a relaxed substrate. Like the substrate material, the materials in the mask layer are preferably compatible with the reagents and conditions of the assays, such as temperature and pH.

With respect to optical density, it may be preferred, when used for high density arrays, that the mask layer substantially reduces or prevents transmission of light of selected wavelengths. The reduction in transmission should be significant enough to effectively increase the signal-to-background ratio provided by the resulting array. It may be preferred that, after relaxation, the optical density of the mask layer 14 is about 0.5 or more for light of selected wavelengths, more preferably about 1.0 or more for light of selected wavelengths, still more preferably about 1.5 or more for light of selected wavelengths, and even more preferably about 2.0 or more for light of selected wavelengths. Regardless of the actual optical density of the mask layer 14 (independent of the substrate and any other materials), the pre-relaxation or original optical density of the mask layer 14 is preferably less than the post-relaxation optical density (for light of selected wavelengths).

Optical density of the mask layer 14 can be determined according to the method described in U.S. patent application Ser. No. 09/410,863, filed on Oct. 1, 1999. "Optical density" is determined based on the percent of light transmitted through an article or layer. Optical density (OD) can be determined according to the equation: Optical Density=Log (1/%T) where: %T is the percent transmittance for light of selected wavelengths. For example, an OD of 2 indicates that 1% of the incident light of selected wavelengths is transmitted.

Because the optical density of the mask layer 14 may be wavelength dependent, optical density is described herein in terms of selected wavelengths. Those selected wavelengths may include one or more specific wavelengths or ranges of wavelengths.

The mask layer 14 may, in some instances, transmit light outside of the wavelengths that could significantly negatively affect detection of an electromagnetic signal emitted from an analyte in response to excitation energy incident on the array 10. For example, the mask layer 14 may exhibit an optical density for the excitation energy that is sufficiently high such that little or none of the excitation energy passes through the mask layer to the substrate 12. As a result, the excitation energy is substantially prevented from exciting materials in the array 10 other than the desired analyte.

In one alternative, the mask layer 14 may transmit the excitation energy or a significant portion thereof, but exhibit a relatively high optical density for light in the wavelengths of the electromagnetic signal generated by the desired analyte as bound to the array in the assaying technique. In other words, any electromagnetic signal, e.g., fluorescence, that could be attributed to the substrate's interaction with the excitation energy would be substantially blocked from transmission to a detector located above the front side of the array 10 by the mask layer 14. As a result, the detector would primarily detect the electromagnetic signals generated by excitation of the desired analyte on the array 10.

The optical densities for the mask layer 14 discussed above are for the arrays 10 after relaxation of the substrate 12. It is, however, preferred that the mask layer 14 be provided before the substrate 12 is relaxed. As a result, the original optical density of the mask layer 14 as provided before relaxation of the substrate 12 will typically be lower than the optical density of the mask layer 14 after relaxation of the substrate 12. In other words, relaxation of the substrate 12 may be useful to increase the optical density of the mask layer 14.

In many instances, the mask layer 14 thickness may correlate to original optical density. Likewise, a thicker mask layer 14 (as deposited) may excessively constrain or reduce shrinkage of the substrate 12 during relaxation such that the desired density of binding sites 16 cannot be obtained after relaxation. By providing the mask layer 14 with a lower original optical density and correspondingly lower thickness, the resistance to shrinkage or reduction in the substrate surface area during relaxation will typically be lower as compared to a thicker mask layer 14. As a result, a thinner, less optically dense mask layer 14 may offer improved performance as compared to a thicker mask layer 14 with a higher original optical density.

It is believed that thicker mask layers 14 may result in larger-dimensioned undulations because the flexural rigidity of the mask layer 14 will increase as its thickness increases. In theory, a flexurally stiffer layer would be expected to bend at a larger radius than that of an object of less rigidity (all other variables being equal). In practice, the flexural rigidity will also be affected by the adhesion properties of the mask layer 14 with respect to the substrate 12.

The mask layer 14 may take a variety of different forms. In one embodiment, the mask layer may take the form of a metal-containing material deposited on the surface 13 of the substrate 12. The metal-containing material may be formed by any known techniques for depositing metal films on substrates, e.g., vapor deposition, sputtering, etc. Alternatively, any other suitable technique for providing a metal-containing material on a substrate may be used. For example, mask layer 14 may be provided in the form of a metal-containing matrix formed on the surface 13 of the substrates 12.

A metal-containing mask layer 14 may include one or more metals, one or more metallic compounds, or combinations of one or more metals and one or more metallic compounds. Examples of suitable metals for the mask layer 14 include, but are not limited to, titanium, chromium, tin, gold, iron, platinum, palladium, silver, and combinations of two or more thereof. Metallic compounds may also be used to form the mask layer 14. For example, the mask layer 14 may include one or more metallic oxides, e.g., titanium dioxide, either in place of metals or in addition to metals. In some instances, it may be preferred that the mask layer 14 consist essentially of one or more metals, one or more metallic compounds, or combinations of one or more metals and one or more metallic compounds.

Another alternative for the mask layer 14 is that it may include one or more inks deposited on the surface 13 of the substrate 12. It may be preferred that the ink be in the form of a curable ink, e.g., an ultraviolet curable ink such as a 100% solids ink. The ink or inks used in the mask layer 14 may include pigments, dyes, synthetic resins, metallic particles, and the like (or any combination of these or other materials), provided that the selected wavelengths of light are not transmitted through the mask layer 14 or their transmission is substantially reduced. If the ink includes dyes, they are preferably non-fluorescent or fluorescent at wavelengths that do not interfere with the assay wavelengths relied on to detect the presence of the desired analytes.

In addition, the surface of the substrate 12 may be treated and/or cleaned to improve attachment of the mask layer 14 to the substrate 12. For example, the substrate 12 may be plasma treated (in, e.g., an oxygen environment) or it may be corona treated. Other treatments may also be used. Further, although not specifically illustrated, additional layers may be introduced between the substrate 12 and the mask layer 14, e.g., tie layers, primers, adhesives, etc., to improve attachment of the mask layer to the substrate.

The mask layer 14 may be provided substantially over the entire area of the surface 13 of the substrate 12, or only portions of the surface 13 of the substrate 12 may include a mask layer 14. In one example of a partially-coated substrate, the mask layer may be provided in discrete, discontinuous areas that may be in a regular or irregular pattern on the surface of the substrate. In the latter case, upon relaxation of the substrate, the topographical surface area of each of the areas including the mask layer will be greater than the projected surface area of those areas. Likewise, the optical density of the mask layer in each of the discrete, discontinuous areas may, after relaxation of the substrate, be increased over the original optical densities in those areas.

Although the mask layer 14 is illustrated herein as including a single, homogenous layer, it should be understood that the mask layer 14 may alternatively be provided as two or more sub-layers of the same or different materials.

Optional Electromagnetic Energy Sensitive Layers

With reference to FIG. 1, the optional layer 14 can alternatively be an electromagnetic energy sensitive material, which may be the same or different than the material of the mask layer. The layer 14 including electromagnetic energy sensitive material that is provided on the substrate can take a variety of forms as described in U.S. patent application Ser. No. 09/459,418, filed on Dec. 9, 1999. Examples of some suitable materials may include those described in U.S. Pat. No. 5,278,377 (Tsai); U.S. Pat. No. 5,446,270 (Chamberlain et al.); U.S. Pat. No. 5,529,708 (Palmgren et al.); and U.S. Pat. No. 5,925,455 (Bruzzone et al.).

Although the layer 14 is depicted as being in direct contact with the substrate 12, one or more intervening layers may be located between the layer 14 and substrate 12 provided that the electromagnetic energy sensitive material in the layer 14 is in thermal communication with the heat-relaxable material in the substrate 12 such that thermal energy in layer 14 is conducted to the substrate 12.

Regardless of its specific form, however, the electromagnetic energy sensitive material in the layer 14 absorbs electromagnetic energy and converts the incident electromagnetic energy into heat such that the thermal energy of the electromagnetic energy sensitive material increases. That thermal energy is then transmitted to the heat relaxable material of the substrate 12 (typically through conduction). The thermal energy raises the temperature of the heat-relaxable material in the substrate. The amount of relaxation is dependent upon the heat-relaxable material in the substrate 12, the temperature to which the heat-relaxable material is heated, and whether the substrate 12 is constrained during heating and/or subsequent cooling.

The heat-relaxable material is preferably raised to at least its relaxation temperature. As defined herein, the relaxation temperature is the temperature at which a desired amount of relaxation is obtained.

Where the electromagnetic energy is to be provided in the form of microwave energy, any one or more of three phenomena may result in the conversion of the microwave energy to thermal energy. Those phenomena include dielectric heating due to electric dipole interaction with the electric field component of the incident microwave energy. Another phenomenon that may be involved in the energy conversion is resistive heating, in which the oscillating electric field component of the incident microwave energy interacts with conduction band electrons in the material. Yet another phenomenon that may be experienced is magnetic heating, in which magnetic dipole interaction of the material with the oscillating magnetic field component of the incident microwave energy heats the material.

One characterization of an electromagnetic energy sensitive material used in connection with the present invention can be based on the dielectric loss factor of the electromagnetic energy sensitive material. In general, the relative dielectric loss factor of a material indicates the ability of the material to generate thermal energy via friction in an oscillating electromagnetic (microwave) field. For most arrays of the present invention, the materials used for the substrate 12, e.g., oriented polymers, do not, alone, show any appreciable relaxation when exposed to electromagnetic radiation such as microwaves or RF energy.

For example, the electromagnetic energy sensitive material will typically possess a relative dielectric loss factor that is greater than the relative dielectric loss factor of the heat-relaxable material of the substrate 12. In such a configuration, the thermal energy of the electromagnetic energy sensitive material will increase more rapidly than the thermal energy of the heat-relaxable material when subjected to microwave energy (understanding that the thermal energy of the heat-relaxable material and other constituents in the substrate 12 may not increase at all upon exposure to microwave energy). As the thermal energy of the electromagnetic energy sensitive material increases, at least a portion of the thermal energy is transmitted to other materials in the contact with the electromagnetic energy sensitive material.

As illustrated in FIG. 1, electromagnetic energy sensitive material can be provided as a part of the array 10 in the form of a layer 14, substantially all of which is an electromagnetic energy sensitive material. In other words, the layer 14 may consist essentially of an electromagnetic energy sensitive material. For example, the layer 14 may be metallic, e.g., it includes one or more metals, one or more metallic compounds, or combinations of one or more metals and one or more metallic compounds. The metals or metallic compounds of layer 14 are preferably of the type that absorb electromagnetic energy and convert that energy into thermal energy. It may also be a "curie point material" (i.e., a magnetic material having a Curie temperature sufficiently high to raise a "heat-relaxable" material to or above its relaxation temperature when exposed to electromagnetic energy).

Where layer 14 is metallic, the composition and/or thickness of the layer may be selected, at least in part, on the frequency of electromagnetic energy to be used to heat the substrate 12. Where microwave energy is to be used, it may be preferred that the metallic layer be relatively thin. If the metallic layer is too thick, it may crack and cause arcing during heating of the substrate 12 or it might not heat sufficiently to relax the substrate. Another consideration in selecting the thickness of a metallic layer 14 is that a layer that is too thick may constrain the substrate 12 from relaxing in response to the application of thermal energy.

In some embodiments where layer 14 is metallic and microwave energy is to be used as the energy source, it may be preferred that the layer 14 be, e.g., about 100 Angstroms thick or less. Another manner in which to characterize the thickness of the layer 14 is by the optical density of the layer, typically measured before the arrays are relaxed. For example, it may be preferred that the optical density of the layer 14 on the substrate 12 be about 0.5 or less before relaxation, optionally even more preferably about 0.3 or less.

If the thermal energy is to be supplied to the array 10 in the form of RF energy and the layer 14 is metallic, it may be thicker than if microwave energy was to be used to heat the substrate 12. The upper limit of any metallic layer to be used for RF induction will typically be controlled by the propensity of thicker metallic layers to prevent or constrain the array from relaxing in response to heating.

Although illustrated as a generally continuous layer 14 on the substrate 12, it should be understood that the thickness of the layer 14 may vary to provide improved control over the amount of electromagnetic energy converted to thermal energy (and, thus, available for transfer to the substrate 12). Another alternative for controlling the conversion process includes providing layer 14 in a discontinuous pattern on the substrate 12. In some instances, it may be desirable to provide both variations in thickness and a discontinuous pattern to improve control over the relaxation process.

The arrays manufactured by the methods of the present invention are useful in a variety of applications, including without limitation, gene sequencing, monitoring gene expression, gene mapping, disease detection, drug discovery, and combinatorial chemistry. One skilled in the art will recognize that the methods of the present invention may be adapted for use on a mass production basis.

EXAMPLES

The following examples have been selected merely to further illustrate features, advantages, and other details of the invention. It is to be expressly understood, however, that while the examples serve this purpose, the particular ingredients and amounts used as well as other conditions and details are not to be construed in a matter that would unduly limit the scope of this invention.

Example 1

This example illustrates the application of glass-like (DLG) thin films to an oriented polyethylene shrink film.

Four samples containing DLG films on shrink films, Samples A–D, were prepared in a commercial Plasmatherm (Model 2480) reactive ion etcher powered by an adjustable 3 kWatt RF power supply and matching network operating at a frequency of 13.56 MHz. The system was pumped by a 5.4 $m^3$/min (200 cfm) roots blower backed by a mechanical pump to a base pressure of less than 10 mTorr before starting the runs.

Plasma treatment was done in three steps in all the runs. The flow rate of the process gases was maintained with either a needle valve or a mass flow controller. Chamber pressure was measured by using a capacitance manometer. In the first step, samples of 1-mil heat shrink polyethylene film (available as Cryovac D955 from Sealed Air Corporation, Saddle Brook, N.J.) were mounted on a 22-inch circular powered electrode and were primed with a pure oxygen plasma to generate surface free radicals to enable good bonding to the glass-like layer. Oxygen flow rate, pressure and RF power for each sample was about 750 sccm (standard cubic centimeter per minute), about 152 to 167 mTorr, and about 500 Watts, respectively. The exposure time was 30 seconds for Sample A and 60 seconds for Samples B–D. In the second process step, a DLG layer was deposited onto each sample's primed surface. For all four samples, DLG thin films were formed through plasma deposition by feeding a mixture of tetramethylsilane (TMS) and oxygen at flow rates, pressures and RF power as indicated in Table 1. Exposure times and resulting film thickness are also listed in Table 1. Finally, the deposited thin films for Samples A–D were treated in an oxygen plasma to remove elemental and covalently bonded carbon from the surface atomic layers and make the surface hydrophilic. The oxygen flow rate, pressure, and RF power were similar to that used in the first step and the exposure time was at least 2 minutes for each sample.

TABLE 1

| Example | TMS/oxygen (sccm/sccm) | Pressure (mTorr) | Power (Watts) | Time (seconds) | Thickness of DLG Film (Angstroms) |
|---|---|---|---|---|---|
| 1A | 30/750 | 172 | 500 | 15 | 250 |
| 1B | 30/750 | 176 | 500 | 30 | 500 |
| 1C | 30/750 | 174 | 500 | 67 | 1000 |
| 1D | 30/750 | 180 | 500 | 300 | 5000 |

Figure 4:
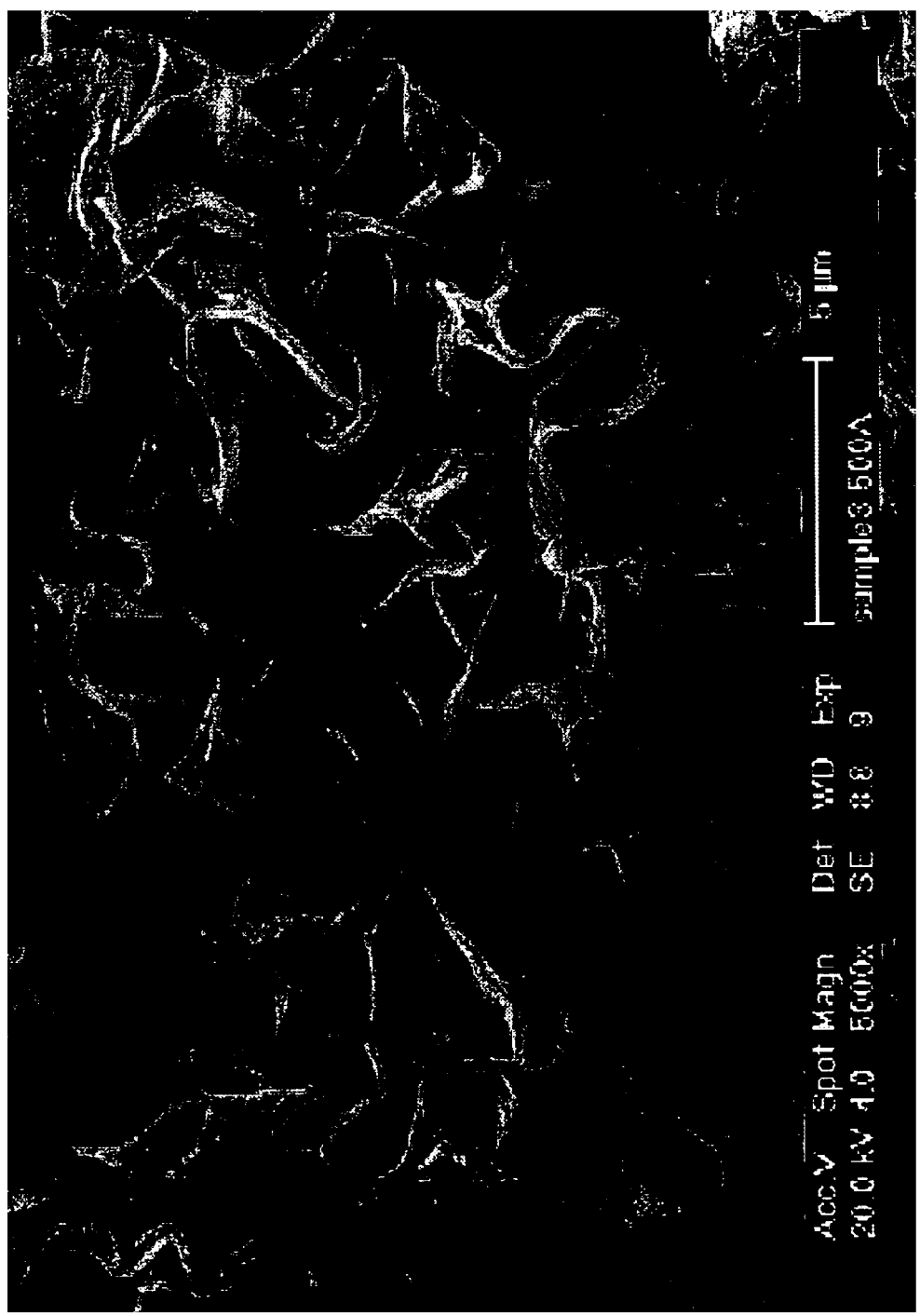
FIG. 4 is a scanning electron micrograph at 5000 magnification of the relaxed surface of a 500 Angstrom thick silicon-containing layer on a relaxed film as prepared in Example 1B.
Figure 5:
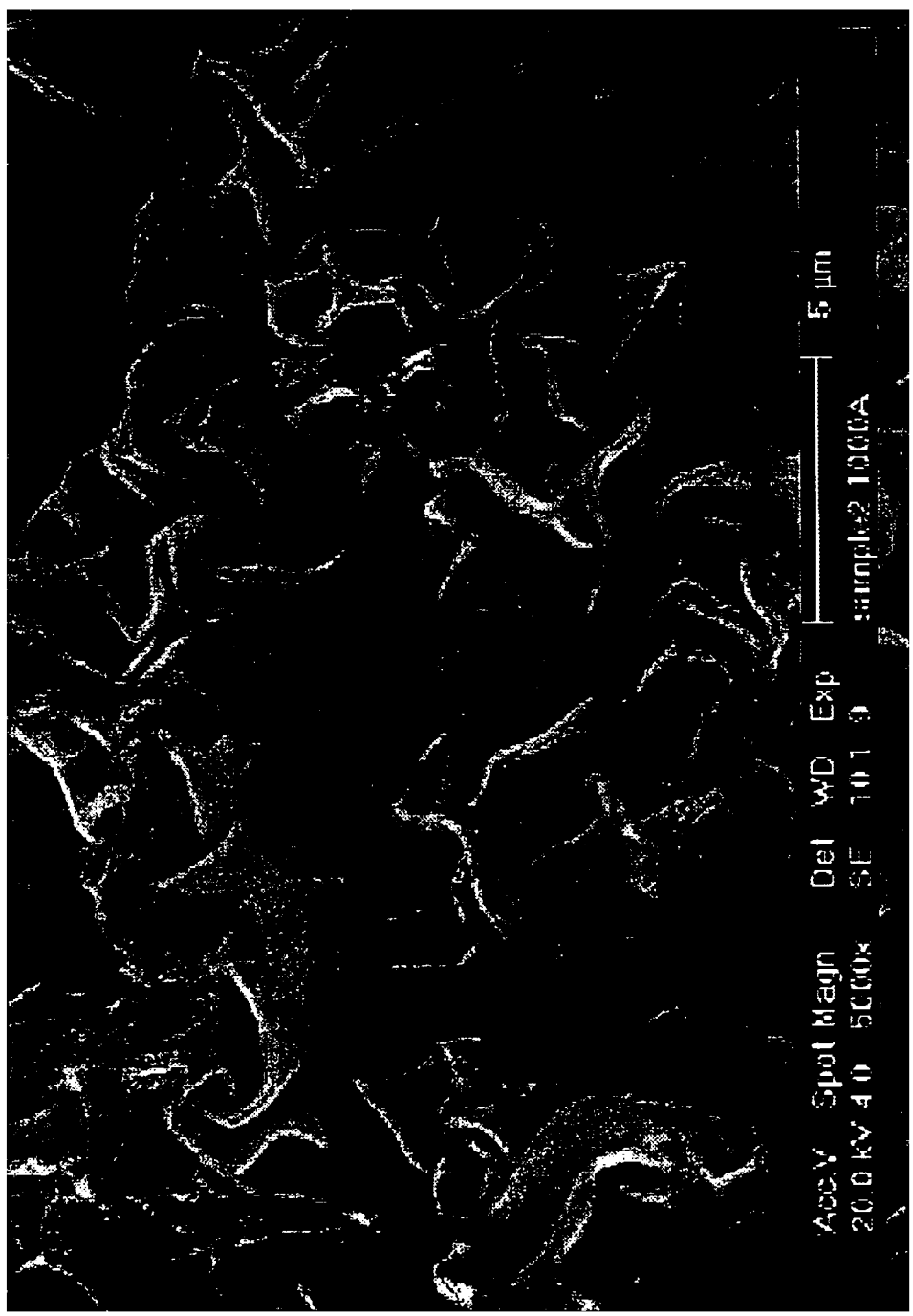
FIG. 5 is a scanning electron micrograph at 5000 magnification of the relaxed surface of a 1000 Angstrom thick silicon-containing layer on a relaxed film as prepared in Example 1C.

Square pieces of the Samples A–D, each about 10 cm by 10 cm, were relaxed on a Corning Model PC-400 hot plate heated to a surface temperature of approximately 155° C. As expected all the films shrunk down to about 4% of their original area. None of the DLG films came off the substrates as observed by light microscopy. The surfaces appeared clouded but uniform to the unaided eye. Under light microscopic examination of the diamond-like film showed visible undulations. The films were then examined by scanning electron microscopy (SEM) (Philips XL30 SEM, Philips, Peabody, Mass. 91960). The elemental detection system (EDAX DX4 microanalyzer, EDAX Corp. Mahwah, N.J. 07430) on the SEM was used to analyze the elemental composition of the coated surfaces. SEM images of the DLG films of Sample B–D before shrinking were smooth and featureless. SEM images at 5000 magnification of the surface of Sample B–D after shrinking are illustrated in FIGS. 4–6, respectively.

As can be seen, the substrates with the 500 and 1000 Angstrom thick DLG films shrunk with the diamond-like film taking on the highly undulated form typically seen when the polyethylene shrink film substrate had been coated with a metal or polymeric coating. However, the substrate with the 5000 Angstrom DLG film of Sample D appeared shattered into small fractured plates. All three DLG films could not be removed from the shrunk substrate by scraping the surface with a hand held scalpel. The elemental analysis surface scan of the samples (A–D) with the SEM showed the presence of silicon and oxygen atoms in a uniform distribution.

The DLG thin film on the polyethylene shrunk substrate were further shown to be able to undergo silylation similar to that expected for ordinary silica or glass. Square pieces (about 25 mm by 25 mm) of untreated polyethylene shrink film substrate and Samples IC and ID were placed in vials with 10 mL of Solution One (containing 10 mL of aminopropyltrimethoxysilane (APTMS) mixed with 85 mL of ethanol and 5 mL of water) and rocked gently for one hour. The pieces were then washed with ethanol followed by water and placed in vials with 10 mL of Solution Two (five milligrams of fluorescein isothiocyanate dissolved in 50 mL of 50 mM AMPSO, 3-[(1,1-dimethyl-2-hydroxyethyl) amino]-2-hydroxypropanesulfonic acid, C.A.S. registry number 68399-79-1, Sigma Chemical Co., St. Louis, Mo. 63178 buffer at pH 9.0) and rocked gently overnight. The untreated and treated samples were then extensively washed with water followed by at least three washes with the AMPSO buffer. The pieces were then dried and shrunk on the Corning hot plate as described above. When examined under a fluorescence microscope (Leitz Laborlux D fluorescent microscope using a fluorescein filter pair) the relaxed untreated film had essentially no fluorescence as expected. The two relaxed-treated samples were highly fluorescent indicating that the silylation reaction was successful and an amine attached the silicon-containing layer for reaction with the fluorescien isothiocyanate. A cross section examination of the samples showed that the fluorescence was coming from the coated surface.

Example 2

This example illustrates additional methods for the derivatization of DLG films on substrates.

A silylation solution (Solution A) was prepared by diluting 4 mL of 3-aminopropyltriethoxysilane (APTES) with 36 mL of 95:5 v/v ethanol/water. A second solution (Solution B) was similarly prepared by diluting 4 mL of 3-glycidoxypropyltri-methoxysilane (GPTMS) with 36 mL of the ethanol/water mixture.

Unshrunk square pieces of Sample 1B, about 60 mm by 60 mm, were placed in each of two petri dishes and covered with Solution A or Solution B, respectively. These were allowed to stand, with occasional agitation, for 1 hour. The pieces were then rinsed thoroughly with ethanol and allowed to air-dry. The treated films (i.e., those with DLG films thereon), labeled Sample E and Sample F, respectively, were characterized by infrared surface analysis utilizing a Perkin-Elmer 16PC FT-IR equipped with a Multiple Internal Reflection (MIR) Accessory and a 45° crystal of KRS-5. By comparison to the IR spectrum of untreated Cryovac D955, the presence of the DLG film was clearly shown in Sample B by strong absorptions in the 800–1300 cm$^{-1}$ range of the spectrum. Subsequent to reaction with Solution A, additional absorptions were noted in the 3000–3500 cm$^{-1}$ range, near 1550 cm$^{-1}$, and in the fingerprint region of the spectrum of Sample E, indicative of reaction of the aminosilane with the DLG film.

A copolymer of 70:30 w/w dimethylacrylamide/vinyldimethylazlactone was prepared according to the procedure described in Example 10 of WO 99/53319, except that toluene was used as the polymerization solvent in place of 2-butanone. A portion of this copolymer solution was diluted to 5% solids with isopropanol. A piece of Sample E was submerged in this solution and mixed for 10 minutes, then removed and allowed to dry. The dried film was then soaked in fresh isopropanol, with agitation, for 10 minutes to remove unbound polymer. The film was allowed to partially dry, then was placed in a vacuum oven at room temperature overnight to remove all traces of solvent. Infrared analysis clearly indicated the presence of a copolymer coating with new, prominent absorptions at about 1820 cm$^{-1}$ (azlactone carbonyl) and 1640 cm$^{-1}$ (amide carbonyl). This sample of film was labeled Sample G.

Example 3

This example illustrates affixation of DNA to samples of modified DLG on polyethylene shrink film prepared in the previous examples.

A) A 500 bp cDNA was prepared and purified by standard PCR techniques. This was then radiolabeled with $^{33}$P using a commercial kit to provide a labeled cDNA solution of approximately 0.5 ng/µl. A series of standards was prepared from this solution by spotting triplicate 1.0 µl spots each at 1×, 0.1×, and 0.01× concentration on polylysine coated glass microscope slides (Newcomer Supply, Middleton, Wis.). Four 1.0 µl spots at 1× concentration were spotted on a piece of Sample E and allowed to dry. The spotted film was then washed with 1% SDS solution, followed by DI water, and dried. The film and standards were imaged using a Packard Cyclone™ Phosphorimager. Analysis of the images obtained indicated that approximately 30% of the spotted cDNA had been immobilized on the Sample E film. This film was then placed on a hot plate with a surface temperature of 155° C. The film was occasionally flipped with tweezers to provide even heat distribution during the shrink step. After observable shrinkage had ceased (approximately 2–3 minutes), the film was removed from the hot plate and allowed to cool. Reimaging indicated that all of the immobilized cDNA was retained during the shrinking process, but was now contained in an area approximately 1/25 its original area.

B) A solution of 5((5-aminopentyl)thioureidyl)fluorescein (25 micrograms/ml) in 50 mM AMPSO buffer containing 1 M sodium sulfate, pH 9.0, was prepared and labeled Solution C. A second solution, Solution D, was prepared which consisted of 80 ug/ml of a 15-base oligonucleotide containing a primary amine at its 5' end and a fluorescein at its 3' end in 50 mM AMPSO buffer, pH 9.0. Solutions C and D were used to spot pieces of Samples F and G; in each case, 4 spots of 1 µl each were applied using a micropipette. The films were then placed in a covered petri dish humidified by a damp paper towel, and allowed to stand for 4 hours. The films were shrunk as described above, then washed with deionized (DI) water, 1% SDS solution, DI water, and the sulfate-containing AMPSO buffer to remove non-covalently bound reagent. Each film was placed on a glass microscope slide, hydrated with additional AMPSO buffer, covered with a glass cover slip, then imaged using a raster scanning device equipped with a 488 nanometer laser, fluorescein filters, and a photo-multiplier tube. Relative light units (RLU) of each spot were measured and reported as the average of the four spots (Table 2).

TABLE 2

| Sample | F | F | G | G |
|---|---|---|---|---|
| Solution | C | D | C | D |
| Observed RLU | 64,703 | 68,040 | 17,017 | 25,819 |

Example 4

This example illustrates affixation of DNA to DLG film on polyethylene shrink film using procedures analogous to those disclosed in the literature. The treated films (i.e., substrates with DLG films thereon) described above may be used to immobilize DNA oligomers and higher molecular weight DNA molecules, as well as other biologically active molecules such as peptides, proteins, and enzymes.

A) Sample IC was silylated with APTES by the procedure of Example 2. Using the procedure described by Matson, et al., Analytical Biochemistry 217, 306–310 (1994), a dimethoxytrityl-protected nucleotide can be coupled to the amino groups of this modified film via standard phosphoramidite activation. Subsequently, oligonucleotides bound to the DLG film can be synthesized in situ via stepwise deprotection/reaction using standard phosphoramidite reagents and/or synthesizers as described therein.

B) Using the procedures disclosed in U.S. Pat. No. 6,013,789, oligonucleotides or nucleic acids having a terminal phosphate can be coupled to the amino groups of Sample E using a carbodiimide in the presence of a substituted imidazole. These methods are amenable to the production of DNA arrays.

C) Using procedures disclosed in Example 1, U.S. Pat. No. 5,919,626, unmodified oligonucleotides or nucleic acids can be immobilized using the epoxy functionality of Sample F.

The preceding specific embodiments are illustrative of the practice of the invention. This invention may be suitably practice in the absence of any element or item not specifically described in this document.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An array comprising:
    a polymeric substrate comprising a relaxed oriented film or a recovered elastomeric material;
    a diamond-like glass film having a first surface and a second surface generally opposed to the first surface with at least a portion of the second surface in contact with at least a portion of the substrate, the first surface of the diamond-like glass film having a projected surface area and a topographical surface area wherein the topographical surface area is greater than the projected surface area; and
    a reactant affixed to the diamond-like glass film.

2. The array of claim 1 wherein linking agents are disposed on at least a portion of the diamond-like glass film.

3. The array of claim 2 wherein the linking agents are covalently bonded to the diamond-like glass film.

4. The array of claim 1 further comprising a binding site that comprises the reactant affixed to the diamond-like glass film.

5. The array of claim 4 comprising a plurality of binding sites.

6. The array of claim 5 wherein a first binding site comprises at least one reactant that is different than at least one reactant of a second binding site.

7. The array of claim 1 wherein the diamond-like glass film comprises oxygen and carbon atoms.

8. The array of claim 1 wherein the diamond-like glass film comprises an undulated surface.

9. The array of claim 1 wherein the substrate comprises a heat shrink film.

10. The array of claim 1 further comprising a mask layer.

11. The array of claim 10 wherein the mask layer is disposed between the substrate and the diamond-like glass film.

12. The array of claim 1 further comprising a layer comprising an electromagnetic energy sensitive material in thermal communication with the substrate.

13. The array of claim 1 wherein the diamond-like glass film has an extinction coefficient of less than 0.010 at 250 nm.

14. The array of claim 13 wherein the diamond-like glass film has an extinction coefficient of less than 0.002 at 250 nm.

* * * * *

UNITED STATES PATENT AND TRADEMARK OFFICE
CERTIFICATE OF CORRECTION

PATENT NO. : 6,881,538 B1
DATED : April 19, 2005
INVENTOR(S) : Haddad et al.

It is certified that error appears in the above-identified patent and that said Letters Patent is hereby corrected as shown below:

Column 8,
Line 41, delete the word "nitrites" and insert in place thereof -- nitriles --.

Column 16,
Line 52, delete the word "azlactone" and insert in place thereof -- azlactones --.

Column 23,
Line 6, delete the word "Coming" and insert in place thereof -- Corning --.

Signed and Sealed this

Twenty-first Day of June, 2005

JON W. DUDAS
*Director of the United States Patent and Trademark Office*